United States Patent
Chicorel

(10) Patent No.: US 6,192,345 B1
(45) Date of Patent: Feb. 20, 2001

(54) COMPUTER KEYBOARD-GENERATED MEDICAL PROGRESS NOTES VIA A CODED DIAGNOSIS-BASED LANGUAGE

(76) Inventor: Marc Edward Chicorel, 6195 Carroll Dr., West Bloomfield, MI (US) 48322-2225

( * ) Notice: Under 35 U.S.C. 154(b), the term of this patent shall be extended for 0 days.

(21) Appl. No.: 09/237,877

(22) Filed: Jan. 27, 1999

Related U.S. Application Data

(63) Continuation-in-part of application No. 08/744,015, filed on Mar. 21, 1997.

(51) Int. Cl.⁷ .............................. G06F 17/00; G06F 17/60

(52) U.S. Cl. .............................................. 705/3; 235/375

(58) Field of Search ................................ 705/2, 3; 704/9; 128/923; 235/375; 707/534, 537, 540, 531, 532; 706/45, 50

(56) References Cited

U.S. PATENT DOCUMENTS

| | | | |
|---|---|---|---|
| 5,296,688 | * | 3/1994 | Hamilton et al. ..................... 235/375 |
| 5,307,262 | * | 4/1994 | Ertel . |
| 5,737,539 | * | 4/1998 | Edelson . |
| 5,772,585 | * | 6/1998 | Lavin et al. ............................. 705/3 |
| 5,802,495 | * | 9/1998 | Goltra ...................................... 705/3 |
| 5,974,389 | * | 10/1999 | Clark et al. ............................ 705/3 |

OTHER PUBLICATIONS

Trace et al., "An intelligent progress note system for MEDAS", from 3rd annual IEEE symposium on computer–based medical systems, pp. 484–491, 1990.*

Trace et al., "A productive user environment for generating progress notes", from 5th annual IEEE symposium on computer–based medical systems, pp. 486–493, 1992.*

Meldman, "Microprocessor technology for psychiatrists", from IEEE Xplore web site of non–patent literature, pp. 216–220, 1978.*

Ma et al., "An intelligent hypermedia system for generating progress notes and physician reminders", from 6th annual IEEE symposium on computer–based medical systems, pp. 165–170, 1993.*

Inada et al., "Fundamental study on adhesive strength of electrical conductive adhesives (ECAs)", from 1998 International symposium on advanced packaging materials, pp. 268–271, 1998.*

Tasukamoto et al., "Electrical aging of adhesive", from IEEE Xplore web site of non–patent literature, pp. 168–172, 1998.*

Greenberg, David S.; The Application of future technologies to medical informatics. Physical Executive, v20, n1, p5 (5),Jan. 1994, USA.

(List continued on next page.)

*Primary Examiner*—James P. Trammell
*Assistant Examiner*—Cuong H. Nguyen

(57) ABSTRACT

A medical progress note documentation system using an organized "language" of codes (a code consisting of at least two letters of the alphabet), that when entered into a programmed processor in a particular arrangement, will generate a descriptive sentence depicting predetermined, frequently used processes in a medical office. Via a predictable, simple and repeatable "language," a doctor can utilize the base of approximately 350,000 bytes of medical descriptive terminology to construct his/her particular medical progress note. Upon completion of the patient encounter, the doctor proceeds to write a short "code" (at least 2 letters) in the appropriate box on a predesigned form. One the "language" is learned, this process uses approximately 15 to 90 seconds of the doctor's time. The code is then entered into the programmed processor. The descriptive information corresponding to the code is printed, reviewed and signed by the doctor. The printed and signed descriptive text is then entered into the patient's medical chart.

4 Claims, 1 Drawing Sheet

OTHER PUBLICATIONS

Larimore, Walter I.; Jordan, Elizabeth V.; Soap to Snocamp: improving the medical record format; Journal of Family Practice, v41,n4,p393(6); USA.

Wyat, Jeremy Crispin;Data and medical records. (Clinical Data Systems, part 1); The Lancet, v344,n8936,p1543 (5); USA.

* cited by examiner

COMPUTER KEYBOARD-GENERATED MEDICAL PROGRESS NOTES VIA A CODED DIAGNOSIS-BASED LANGUAGE

CROSS REFERENCE

This application is a continuation-in-part of copending U.S. patent application Ser. No. 08/744,015 filed Mar. 21, 1997 having the same title.

FIELD OF THE INVENTION

The invention is related to the field of generating medical progress notes for entry into a patient's file.

BACKGROUND ART

The generation of medical progress notes entered into a patient's file is required for good patient medical care and more recently for payment for rendered medical care from medical insurance companies, Medicare or any other agency. Over the years, the S.O.A.P. format has been developed to achieve continuity and repeatability. S.O.A.P. is an acronym for the four steps used in medical record documentation for a doctor-patient encounter.

S.O.A.P. stands for

Subjective

Objective

Assessment and

Plan.

Currently the individual components of the S.O.A.P. format are handwritten or typed by the physician, dictated, or entered by means of bar coded notes or a voice recognition system. The medical record often lacks continuity and consistency. The time spent in the preparation of the medical documentation detracts from quality time available with the patient. For example, handwriting or dictation of the progress note is obviously the most time consuming of the above-enumerated methods. The bar-coded method requires the doctor to locate the desired sentence or phrase on a wall chart or bar code book having hundreds of words and phrases to choose from. The doctor must then choose the appropriate bar code using a bar code reader to enter the selected word or phrase into a word processor. Current word recognition systems require extremely slow and clearly enunciated speech that can be more time consuming and frustrating for the physician. Like hand written notes, the methods using voice recognition may also result in inconsistencies in describing the same observation assessment or plan for two different patients having the same symptoms.

Computer implementation of various health care procedures and bookkeeping are known in the healthcare industry. For example, Ertel in U.S. Pat. No. 5,307,262 is directed to a method and system to review and control clinical data quality in the reporting of hospital claim data. In particular, as stated in the summary of the Ertel patent, the system utilizes the effeciency of batch operations to analyze claim data or entire groups of patients for the purpose of identifying and correcting both case specific and systematic problems in data quality in the most efficient way possible. Although the system taught by Ertel requires the entry of diagnostic and procedure codes into the system, the codes used by Ertel relate to medical billing and are only used in combination with Medicare's "Diagnosis Related Group" program that assigns a diagnosis-related group and to assign several secondary attributes to the patient data sets along with the actual clinical data being entered. The Ertel system is unrelated to a method of generating office progress notes, of the type entered into a private patient file for the purpose of recording the ongoing events of the doctor-patient relationship in the medical office setting. In the medical office, billing is a separate issue from documentation of the patient's progress.

SUMMARY OF THE INVENTION

The invention is a method for generating medical notes using codes indicative of a patient-doctor encounter. The method begins with the doctor preparing a set of codes and supplementary notations subsequent to the patient-doctor encounter. Each code and supplemental notation identifying a frequently used event in a medical office. The prepared codes and supplemental notations are then entered into a programmed computer to generate printable progress notes identified by the entered set of codes and supplementary notations. The program stores the text of the progress notes in sentence form. The stored text of the progress notes being addressable by the codes and supplementary notations. The printed progress notes are then reviewed by the doctor and after his signature approval, entered into the patient file.

In the preferred embodiment, the printed medical progress notes are prepared using the standard S.O.A.P. format. In an alternate embodiment, the medical progress notes are printed on an adhesive-backed paper and pasted on an existing page in the office patient file.

An object of the invention is to provide a method for markedly reducing the time required to generate medical progress notes.

Another object of the invention is to provide a thorough and universally acceptable description of a doctor-patient encounter.

Yet another object of the invention is to provide easily adaptable (customizable) progress notes describing a doctor-patient encounter.

Another object of the invention is that the codes are a natural expression of the doctor via a simple "thought process."

Still another object of the invention is to allow the doctor to function, for the most part, without having to memorize or look up the codes on a chart. This is feasible via the use of codes designed on a basis of a logical "thought-process format" alluded to in the previous paragraph.

These and other objects of the invention will become apparent from a detailed reading of the Specification.

BEST MODE FOR CARRYING OUT THE INVENTION

Figure 1:
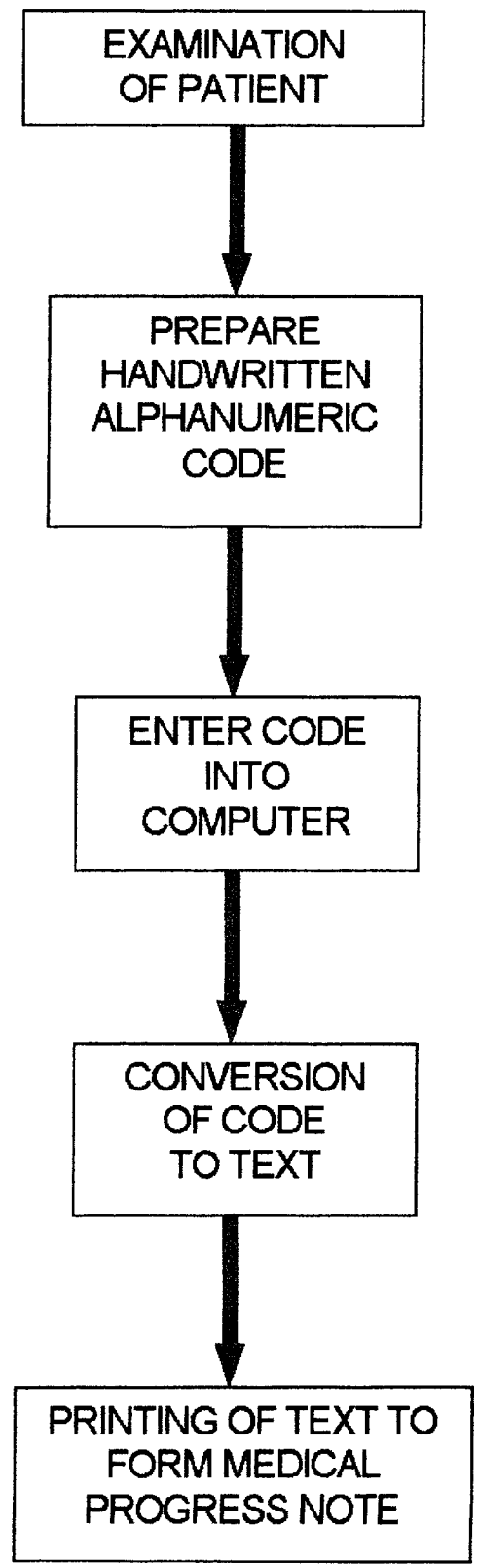
FIG. 1 is a flow diagram of the process for the guardian of medical progress notes.

The method consists of systematically generating an organized set of at least two letter codes indicative of a patient-doctor encounter which when entered into a programmed computer or microprocessor system will generate humanly readable medical progress notes in the form of descriptive phrases and sentences depicting the most frequently used processes in a medical office. The programmed computer stores the full text of the progress notes, which are individually addressable by the entered codes and supplementary notations.

Continuity and repeatability of the printed medical progress notes is achieved via the use of a specific format for documentation of ongoing patient progress in the medical record. The particular format that is taught in medical schools, nursing schools, internships and residency programs as the appropriate method for documentation in the patient medical progress note is referred to as the S.O.A.P. format for medical documentation. HCFA (Health Care Financing Administration) and many medical insurance companies require the S.O.A.P. format as the preferred format for medical documentation. The S.O.A.P. format is designed to be inclusive of all components of the doctor-patient encounter while providing the ability to gain quick reference to any of the individual components of each encounter. The documentation of each doctor-patient encounter consists of four or five components depending upon whether or not a treatment has been rendered. The documentation of a doctor-patient encounter in accordance with the invention, using the S.O.A.P. format is as follows:

Subjective: The patient's complaint, the reason for the visit (in the patients own words).

Objective: A description of the objective findings (signs/symptoms).

Assessment: Most often a diagnostic or "working" diagnostic label of the presented Condition. An assessment as to what is actually taking place.

Tx: Treatment rendered.

Plan: A brief description of the plan to manage the patient's needs.

The method disclosed herein uses the S.O.A.P. format in the following manner:

Each of the two (or more) letter codes begins with the letters S, O, A, TX, P or Z. The "Z" codes represent commonly used adjunctive terms or phrases. These codes, when entered into a programmed computer, address the appropriate stored medical progress note and outputs the stored descriptive sentence reflective of the appropriate component of the S.O.A.P. format, the output progress note relating specifically to that particular doctor-patient encounter. A word processor system print the medical progress notes addressed by the codes, supplemented by the appropriate supplementary notations. These printed medical progress notes are subsequently entered into the patient's chart or file.

Initially, in the development of the method according to the invention, the programmed computer was an IBM compatible computer programmed with the word processor program entitled Microsoft Word,, designed for use with the application entitled Windows 3.11. However, any computer programmed with any comparable software can be used. A Microsoft Word for Windows with "Autocorrect," was the component of the word processor program used, however any comparable word processor program component may be used.

The medical progress notes themselves, receive their continuity from the S.O.A.P. format. The flow of the coding language is designed so that the physician will not have to memorize the codes but will naturally express himself/herself via a simple thought process. The "O.," "A.," "tx." and many of the frequently used "S." components of the code are "diagnostic-based." Each code according to the invention, begins with one of the six letters, "S," "O," "A", "tx," "P," or "Z." The remaining letters in each code are indicative of the actual diagnosis. Two letters are used whenever possible unless the diagnosis contains several syllables or words. In these cases a third, fourth (or greater) letter is appropriate. The first letter in each code identifies the S.O.A.P. (and bc, or Z) component of the medical progress note. The following example demonstrates typical examples of the structure of the code according to the invention. In this example, a patient suffering from "bursitis" presents himself to the physician. The resulting set of codes to be entered into the programmed computer is as follows:

SCO=Patient complains of (the subjective complaint is entered as a fourth letter or verbatim sentence in the patient's words).

OB=Inflamed bursa is noted. Mild peripheral inflammation w/ no proximal cellulitis or edema. No open lesions. (+) pain on direct palpation. A "Z" code will describe the anatomical location at this point in the descriptive sentence . . . eg: ZD=dorsal, ZPI=proximal interphalangeal joint. At this point, the specific toe and foot are entered, for example "3R"=$3^{rd}$ digit, right foot.

AB=Bursitis

TXBD=Needle-aspirate inflamed bursa. Betadine prep, Dexamethasone phosphate, B12, 1% lidocaine plain (¼, ¼, ½ cc) Again, a "Z" code will describe the anatomical location (eg: ZPI=proximal interphalangeal joint), 3R.

PI=Instructions given

The method generating medical progress notes via coded language is as follows:

A doctor-patient encounter occurs.

Doctor writes codes and supplementary abbreviations on a progress note routing slip.

An assistant or even the doctor him/herself enters the patients name and the set of codes into the programmed computer.

Programmed computer converts the set of codes into appropriate statements or sentences, and generates human readable medical progress notes.

The medical progress notes are subsequently reviewed and signed by the doctor.

The signed medical progress notes are then entered into the parents file (chart) as a permanent record of that particular doctor-patient encounter.

Preferably, the printed medical progress notes are printed on an 8½×11" adhesive-backed paper which after review and signature by the doctor, may be cut to the appropriate size and pasted into the patients file. Optionally, the medical progress notes may be printed on an 8½×11" sheet of paper without adhesive backing. Using this adhesive paper method, multiple separate successive sets of medical progress notes can be entered on one page of the patient's file.

An example of a common documentation scenario taken from a doctor-patient encounter in the office of a dermatologist, internist podiatrist, or any other physician licensed to perform the described procedure, is given below:

Mary Jones, a patient, presents with a painful ingrown toenail of the medial (inside) border of the hallux (first toe). The appropriate set of coding according to the invention would be as indicated below. The set of codes would initially be hand written by the doctor on a Progress Note Router Form:

| | |
|---|---|
| Mary Jones | 10/11/96 |
| SIG ZM 1L | |
| OIG₁ ZM 1L | |
| AIGA ZM 1L | |
| TXIGS ZM 1L | |
| PRX ZGMO. PIW. | |

The above set of codes when entered into the programmed computer would be decoded and appear on the screen of the monitor as follows:

Oct. 11, 1996 Jones, Mary

S C/o tenderness at nail border medial 1 L

O Incurvated, mildly inflamed, non-draining nail border w/ point tenderness noted. Mild hypertrophy of nail fold medial 1 L A Acute ingrown nail medial 1 L tx: Simple, partial nail avulsion (to proximal nail fold): 1% Lidocaine plain, TAO, DSD medial 1 L P Prescription written: Geritamicin ointment Written instructions given.

This information, now appearing on the monitors screen would subsequently be printed out and entered into the patient's file, after approval by the doctor. As indicated above, if the progress notes are printed on adhesive-backed paper, the adhesive backed paper would be cut to size and mounted on an existing page in the patient's file.

Preparation of the medical progress notes is done in-house with a marked increase of effeciency of the doctor's time due to the significant reduction of the number of words that need to be written by the doctor or the number of words required to be entered into the programmed computer by an assistant, when the progress notes are voice recorded. The method according to the invention, can reduce the time required to prepare the exact wording of the medical progress notes by up to 97%. The time spent by the doctor in the actual communication of the information is considerably diminished relative to handwritten, bar coded and voice recorded methods and at least equal to or less than conventional dictation.

The medical documentation method described herein, can prove to be significantly more reliable than handwritten, dictation or voice recognition methods, because with those methods, there is the potential for failure of the doctor to be totally inclusive of the pertinent information. Ever-present efforts to minimize patient waiting time as well as other time restraints in a busy medical office can frequently induce a less-than-complete medical progress note. The method for generating medical progress notes disclosed herein contains a thorough portrayal in didactic medical terminology, of the intended description in the form that it most commonly presents in that specialist's medical office. Also, the method provides for the customization of the progress notes to meet the doctor's individual needs and style of practice.

A potential problem with some of the other computerized progress note methods previously discussed, would be one of repeatability. An insurance auditor may review such repeating sentences as "canned phrasing" that could be interpreted as simple reoccurring verbiage, not totally reflective of that particular doctor-patient encounter. As is true in any type of work-related activity, it is simply human nature for us to develop modifications of generalized techniques with which we feel comfortable. For example, a carpenter will generally follow the same basic technique for "roughing-in" a house, but employing small personal adaptations along the way that work for him. A short-order cook or a thoracic surgeon would probably agree that they carry out their work, for the most part, utilizing a particular set of criteria and techniques for a given task each time they perform that task. But cook A might vary slightly in technique from cook B, and surgeon A from surgeon B. These subtle variances require that the concept of customization, unique to all of us, and no matter on how small a scale, is preferable in the workplace, and is what allows each of us to maintain some degree of individuality.

To avoid "canned" medical progress notes, the disclosed method is customizable at either of the basic levels: the codes themselves and the associated descriptive text. The codes and the actual descriptive text, since both are generated by the doctor to meet his/her needs and his/her own style and type of practice, vary from doctor to doctor. With the use of "Z" codes, the particular progress notes are further modified in detail, to reflect the site of anatomical involvement as well as any other factors that are pertinent.

Using a predictable, simple, and repeatable "language," a doctor can utilize a base of approximately 350,000 bytes of medical descriptive terminology to construct his or her own particular progress note library. Upon completion of a patient-doctor encounter, the doctor writes a set of short codes, usually 3 or 4 letters per code, in the appropriate boxes on a progress note router form. The router form will contain an appropriate box for each of the components for the S.O.A.P. format plus supplementary notations, ie: the "Z" code or longhand writing. Once the code language is learned, the filling in of the progress note router form utilizes approximately 15 to 90 seconds of the physician's time.

Once the progress note router form is completed by the physician, the content of the progress note router form is entered into the programmed computer which converts the codes and supplementary notations into human readable medical progress notes suitable for entry into the patient's file.

While the invention has been described in detail, it is not intended that the embodiment describes all possible forms of the invention. Rather the words used in the specification are words of description rather than limitation, and it is understood that various changes may be made without departing from the spirit and scope of the invention.

What is claimed is:

1. A method for producing keyboard-generated medical progress notes comprising preparing a set of handwritten alphanumeric codes based on language of abbreviations of didactic medical terminology and supplementary notations subsequent to a doctor-patient encounter, each alphanumeric code and supplementary identifying notation identifying a specific process used in the doctor-patient encounter;

entering the set of alphanumeric codes based on a language of abbreviations of didactic medical terminology and supplementary notations into a programmed processor by means of a keyboard, the programmed processor storing the text of the progress notes in sentence form, the text of the progress notes being addressable by the alphanumeric codes and supplementary notations;

addressing the text of the medical progress notes with the entered set of alphanumeric codes and supplementary notations to generate a set of medical progress notes;

printing the medical progress notes addressed by the alphanumeric codes and supplementary notations; and entering the printed progress notes into the patient's file.

2. The method of claim 1 further including the step of reviewing and signing the printed progress notes by the doctor prior to entering them into the patient's file.

3. The method of claim 1 wherein S.O.A.P. is an acronym for a universal format used in the preparation of medical progress notes, there the letters S, O, A, and P permits the expression of the essence of a doctor-patient encounter as follows:

S=Subjective
O=Objective
A=Assessment (diagnosis)
P=Plan and wherein the set of alphanumeric codes utilize the S.O.A.P. format.

4. The method of claim 1 wherein the printed progress notes are printed on an adhesive-backed paper that may be pasted into the patient's file.

* * * * *